US011459283B2

(12) United States Patent
Mayumi et al.

(10) Patent No.: US 11,459,283 B2
(45) Date of Patent: Oct. 4, 2022

(54) METHOD FOR PRODUCING XYLENE (71) Applicant: ENEOS CORPORATION, Tokyo (JP)

(72) Inventors: Kazuya Mayumi, Tokyo (JP); Hideo Tsuneoka, Tokyo (JP); Yasuyuki Iwasa, Tokyo (JP)

(73) Assignee: ENEOS CORPORATION, Tokyo (JP)

( * ) Notice: Subject to any disclaimer, the term of this patent is extended or adjusted under 35 U.S.C. 154(b) by 0 days.

(21) Appl. No.: 17/272,726

(22) PCT Filed: Aug. 27, 2019

(86) PCT No.: PCT/JP2019/033413
§ 371 (c)(1),
(2) Date: Mar. 2, 2021

(87) PCT Pub. No.: WO2020/050092
PCT Pub. Date: Mar. 12, 2020

(65) Prior Publication Data
US 2021/0347713 A1 Nov. 11, 2021

(30) Foreign Application Priority Data
Sep. 3, 2018 (JP) .............................. JP2018-164601

(51) Int. Cl.
| C07C 6/12 | (2006.01) |
| B01J 29/40 | (2006.01) |
| C07C 2/84 | (2006.01) |
| C07C 4/02 | (2006.01) |
| C07C 5/03 | (2006.01) |

(52) U.S. Cl.
CPC .............. C07C 6/12 (2013.01); B01J 29/405 (2013.01); C07C 2/84 (2013.01); C07C 4/02 (2013.01); C07C 5/03 (2013.01); C07C 2529/40 (2013.01)

(58) Field of Classification Search
CPC . C07C 15/08; C07C 5/2732; C07C 2529/068; C07C 2529/40; C07C 2/76;
(Continued)

(56) References Cited

U.S. PATENT DOCUMENTS

| 4,278,827 A | 7/1981 | Chu et al. |
| 4,642,402 A | 2/1987 | Jensen |

(Continued)

FOREIGN PATENT DOCUMENTS

| EP | 0 493 040 A2 | 7/1992 |
| JP | S56-145227 A | 11/1981 |

(Continued)

OTHER PUBLICATIONS

Oct. 21, 2019 Search Report issued in International Patent Application No. PCT/JP2019/033413.

*Primary Examiner* — Sharon Pregler
(74) *Attorney, Agent, or Firm* — Oliff PLC (57) ABSTRACT

A method for producing xylene, including a conversion reaction step of bringing a raw material containing a light hydrocarbon having 2 to 7 carbon atoms as a main component into contact with a crystalline aluminosilicate-containing catalyst to produce a product containing a monocyclic aromatic hydrocarbon having 6 to 8 carbon atoms and a xylene conversion step of subjecting the product to a disproportionation reaction or a transalkylation reaction.

11 Claims, 3 Drawing Sheets

(58) Field of Classification Search
CPC .... C07C 2/84; C07C 4/02; C07C 5/03; C07C 5/2729; C07C 5/417; C07C 6/12; B01J 29/405; B01J 2229/26; B01J 2229/42; B01J 29/26; B01J 29/40; B01J 29/44; B01J 29/65; B01J 29/70; B01J 29/87; B01J 29/89

See application file for complete search history.

(56) References Cited

U.S. PATENT DOCUMENTS

| | | | |
|---|---|---|---|
| 5,609,751 A * | 3/1997 | Wall | C07C 5/417 |
| | | | 208/133 |
| 10,308,567 B2 * | 6/2019 | Jin | C07C 2/76 |
| 2014/0200377 A1 | 7/2014 | Yanagawa et al. | |

FOREIGN PATENT DOCUMENTS

| | | |
|---|---|---|
| JP | S62-190132 A | 8/1987 |
| JP | H05-058919 A | 3/1993 |
| JP | H08-119882 A | 5/1996 |
| JP | 2008-037803 A | 2/2008 |
| JP | 2008-038032 A | 2/2008 |
| JP | 2009-233601 A | 10/2009 |
| JP | 2012-240998 A | 12/2012 |
| JP | 2015-531405 A | 11/2015 |
| JP | 2018-030112 A | 3/2018 |
| WO | 2014/058465 A1 | 4/2014 |
| WO | 2017/052858 A1 | 3/2017 |

* cited by examiner

METHOD FOR PRODUCING XYLENE

TECHNICAL FIELD

The present invention relates to a method for producing xylene.

Priority is claimed on Japanese Patent Application No. 2018-164601, filed on Sep. 3, 2018, the content of which is incorporated herein by reference.

BACKGROUND ART

Conventionally, catalytic reforming of straight naphtha using a platinum/alumina-based catalyst has been widely adopted as a method for obtaining gasoline or an aromatic hydrocarbon, which has a high octane value. As a raw material naphtha in this catalytic reforming, a fraction having a boiling point of 70° C. to 180° C. is mainly used for the purpose of producing gasoline for automobiles. In addition, in the case of producing aromatic fractions such as benzene, toluene, and xylene, so-called BTX, a fraction of 60° C. to 150° C. is used.

However, as the number of carbon atoms of the raw material hydrocarbon decreases, the conversion rate to aromatics decreases, and the octane value of the product also decreases. Therefore, in the conventional catalytic reforming method in which a light hydrocarbon containing a hydrocarbon having 7 or fewer carbon atoms as the main component has been used as a raw material, it has been difficult to produce gasoline having a high octane value and an aromatic hydrocarbon in high yield. As a result, the use of such light hydrocarbons has been limited to petrochemical raw materials and raw materials for producing city gas.

For this reason, attempts have been made to produce an aromatic hydrocarbon from the light hydrocarbon. For example, Patent Documents 1 to 3 disclose a method for producing an aromatic hydrocarbon by using a hydrocarbon having 2 to 7 carbon atoms as the main raw material and a gallium-containing crystalline aluminosilicate catalyst composition.

It is preferable that a monocyclic aromatic hydrocarbon having 6 to 8 carbon atoms, which has a high added value, can be produced in high yield. However, the method for producing an aromatic hydrocarbon using a hydrocarbon having 2 to 7 carbon atoms as the main raw material has a problem in that profitability is low because the yield of toluene, which is cheaper than benzene or xylene, is high. In recent years, the demand for xylene sometimes exceeds the demand for benzene or toluene due to an increase in the demand for terephthalic acid. In that case, it is preferable to produce, particularly, xylene as a monocyclic aromatic hydrocarbon having 6 to 8 carbon atoms in a yield higher than that of benzene or toluene. However, no conventional producing process with which xylene is produced selectively against benzene or toluene has been provided.

CITATION LIST

Patent Document

[Patent Document 1]
Japanese Unexamined Patent Application, First Publication No. 2008-37803
[Patent Document 2]
Japanese Unexamined Patent Application, First Publication No. 2008-38032 [Patent Document 3]
Japanese Unexamined Patent Application, First Publication No. 2009-233601

SUMMARY OF INVENTION

Technical Problem

The present invention has been made in consideration of the above circumstances, and an object of the present invention is to provide a method for producing xylene in high yield by using, as a raw material, a light hydrocarbon containing a hydrocarbon having 7 or fewer carbon atoms as the main component.

Solution to Problem

The first aspect of the present invention is a method for producing xylene, including a conversion reaction step of bringing a raw material which contains a light hydrocarbon having 2 to 7 carbon atoms as a main component into contact with a crystalline aluminosilicate-containing catalyst (Z) to produce a product containing a monocyclic aromatic hydrocarbon having 6 to 8 carbon atoms and a xylene conversion step of subjecting the product to a disproportionation reaction or a transalkylation reaction.

Advantageous Effects of Invention

According to the present invention, a method for producing xylene in high yield by using, as a raw material, a light hydrocarbon containing a hydrocarbon having 7 or fewer carbon atoms as the main component is provided.

DESCRIPTION OF EMBODIMENTS

First Embodiment

Figure 1:
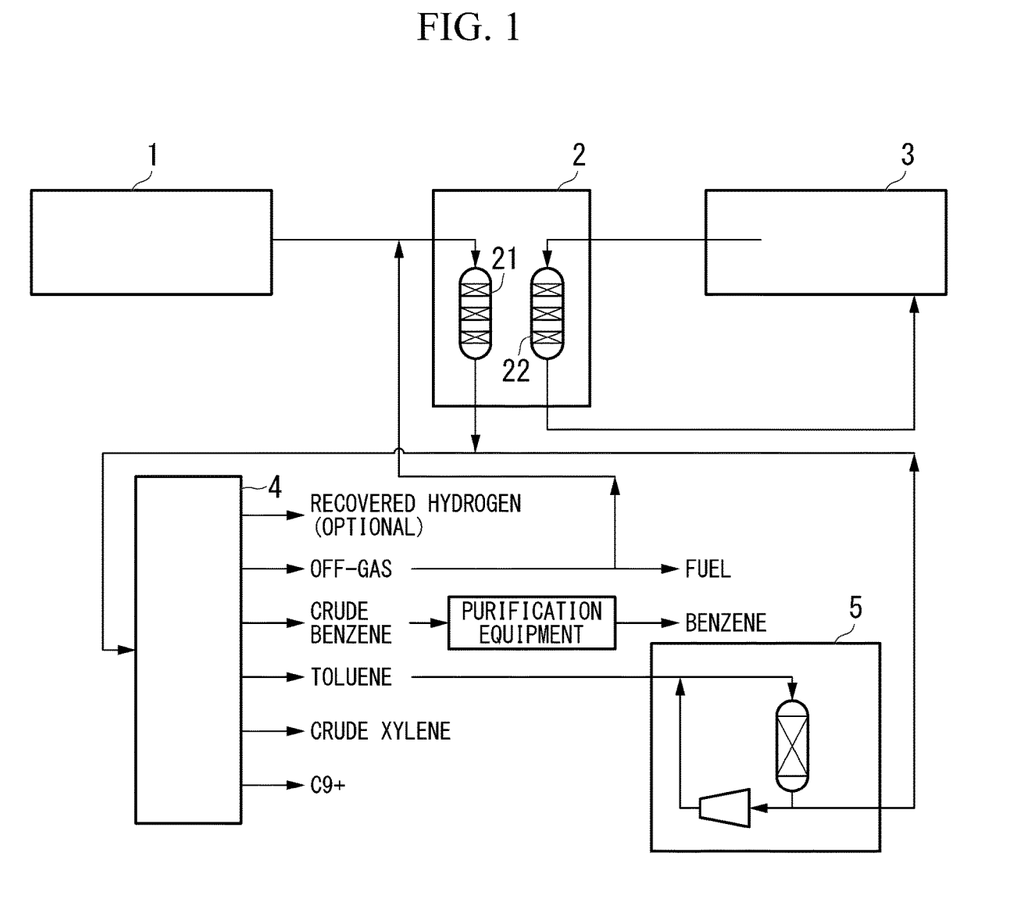
FIG. 1 a diagram for explaining a first embodiment of a method for producing xylene of the present invention.

As shown in FIG. 1, in the first embodiment of the method for producing xylene of the present invention (hereinafter, may be simply referred to as the "first embodiment"), a raw material 1 containing a light hydrocarbon having 2 to 7 carbon atoms as the main component is brought into contact with a crystalline aluminosilicate-containing catalyst (Z) (hereinafter, may be simply referred to as a "catalyst (Z)") in a conversion reaction device 2, and then a product containing a monocyclic aromatic hydrocarbon having 6 to 8 carbon atoms is produced. Subsequently, the product is subjected to a disproportionation reaction in the disproportionation reaction device 5 to produce xylene.

Specifically, it is preferable that the first embodiment mainly has the following five steps (z1-1) to (z1-5). In addition to the following five steps (z1-1) to (z1-5), the method for producing a monocyclic aromatic hydrocarbon of the present invention may have a step (z1-6).
(z1-1) Conversion reaction step
(z1-2) Gas-liquid separation step of reaction bed effluent
(z1-3) Step of separating hydrogen from separation gas (z1-4) Step of separating aromatic hydrocarbon from separation liquid (Z1-5) Xylene conversion step of subjecting aromatic hydrocarbon to disproportionation reaction (z1-6) Step of mixing raw material light hydrocarbon with recycled gas

[(z1-1) Conversion Reaction Step]

In this step, the raw material 1 containing a light hydrocarbon having 2 to 7 carbon atoms as the main component is supplied to the conversion reaction device 2 in which n pieces of reaction beds retaining at least the catalyst (Z) are arranged in series. The catalyst (Z) will be described later.

A heating furnace or the like is provided between the reaction beds of the conversion reaction device 2 as means for heating an effluent from the reaction bed. The conversion reaction step is a step of passing a mixture of a light hydrocarbon as a raw material with a recycled gas described later through a reaction bed and converting the mixture to an aromatic hydrocarbon. The preferred reaction conditions in this step are a reaction bed inlet temperature of 350° C. to 650° C., a hydrogen partial pressure of 0.5 MPa or less, and a gas space velocity of a raw material of 100 to 2,000 hr$^{-1}$.

The reaction bed inlet temperature in the conversion reaction step (z1-1) according to the first embodiment is generally preferably in the range of 350° C. to 650° C. However, in a case where the light hydrocarbon as a raw material contains normal paraffin as the main component, the temperature is more preferably 450° C. to 650° C., in a case of containing normal paraffin as the main component, the temperature is still more preferably 400° C. to 600° C., and in a case of containing olefin as the main component, the temperature is even still more preferably 350° C. to 550° C.

The reactor that is used in the conversion reaction step (z1-1) is not particularly limited, and examples thereof include a fixed bed type reactor, a CCR type reactor, and a fluidized bed type reactor. In a case where a fixed bed or a CCR type reactor is used, it is preferable that n pieces of reaction beds (n is an integer of 2 or more) retaining the catalyst (Z) are arranged at least in series, and further, a heating device such as a heating furnace is provided between the reaction beds or in the reaction bed as means for heating an effluent from the reaction bed. In a case where the amount of heat absorbed is small, the reaction bed retaining the catalyst (Z) may be one (n=1).

Further, the first reaction bed among n pieces of reaction beds arranged in series is arranged so that the catalyst amount in the first reaction bed is 30% by volume or less of the total catalyst amount, preferably 1% to 30% by volume, more preferably 2% to 30% by volume, and still more preferably 2% to 28% by volume. In a case where the number n of the reaction beds arranged in series is 3 or more, it is preferable that the catalyst amount in the first reaction bed is 60/n % by volume or less of the total catalyst amount. As a result, the final yield of aromatics is improved. The number n of the reaction beds is not particularly limited as long as it is 2 or more; however, in a case where the number is too large, the effect does not change, and the economic efficiency is bad. Accordingly, n is preferably 2 or more and 8 or less and more preferably 3 or more and 6 or less.

Further, in the conversion reaction step (z1-1) according to the first embodiment, the operation can be carried out at the predetermined reaction bed inlet temperature, or the operation can be carried out by continuously or stepwisely raising the reaction bed inlet temperature to obtain the predetermined yield of aromatics. In a case where the yield of aromatics falls below the predetermined range or the reaction bed inlet temperature exceeds the predetermined temperature range, the reactor is switched to a reactor filled with a new catalyst or a reactor filled with a regenerated catalyst, and then the reaction is continued. The regeneration of the catalyst can be carried out, for example in the regenerator 3, by heating treatment at 200° C. to 800° C. preferably 350 to 700, in the air stream such as air, nitrogen, hydrogen, or a nitrogen/hydrogen mixed gas.

The conversion reaction step (z1-1) according to the first embodiment is preferably carried out using two or more series of fixed bed type reaction devices including a reaction bed retaining the catalyst (Z). In this case, each series of reaction devices is composed of a plurality of reaction beds that are arranged in series. The catalyst in one or more series of reactors is subjected to the regeneration treatment while a raw material containing a light hydrocarbon is introduced into the other one or more series of reactors to promote the reaction. With these two or more series of reactors, the reaction operation is carried out for 1 to 10 days using one or more series of reactors, and then the used reactors are switched to other one or more series of reactors that have been subjected to the regeneration treatment, to carry out reaction/regeneration, whereby continuous operation can be carried out, for example, for one year.

For example, in FIG. 1, the catalyst in the reaction bed 22 is subjected to the regeneration treatment while proceeding with the reaction in the reaction bed 21, but after a lapse of a predetermined period, the reaction bed 21 and the reaction bed 22 can be switched to carry out reaction and regeneration.

Further, as in the cyclic operation, it is also possible to switch a part or all of the reactors of the series that are used for the reaction to other series to continue the reaction. Then, it is preferable to raise the reaction temperature continuously or stepwise by about 5° C. to 20° C. for each cycle of the reaction for 1 to 10 days to maintain the yield of aromatics in a predetermined range of 40% to 75% by weight.

The yield R of aromatics is represented by the following formula (1).

$$R = A/B \times 100 (\%) \quad (1)$$

A: Mass of aromatic hydrocarbon having 6 to 8 carbon atoms in conversion reaction product B: Mass of all converted reaction products and unreacted hydrocarbon raw material In a case where an aliphatic and/or alicyclic hydrocarbon is converted to an aromatic hydrocarbon, a reaction involving dehydrogenation proceeds, and thus under the conditions of such a reaction, a hydrogen partial pressure commensurate with the reaction can be obtained without adding hydrogen. The intentional addition of hydrogen has the advantage of suppressing the accumulation of coke and reducing the frequency of regeneration; however, it is not always advantageous because the yield of aromatics decreases drastically as the hydrogen partial pressure increases. For this reason, the hydrogen partial pressure is preferably suppressed to 0.5 MPa or less.

In the conversion reaction step according to the present invention, it is desirable that a light gas containing methane and/or ethane, which is circulated as a recycled gas from the subsequent separation step, is allowed to be present. In a case where the conversion reaction is carried out in the presence of the light gas containing methane and/or ethane, the precipitation of coke on the catalyst can be suppressed, and thus the yield of aromatics can be maintained high for a long period of time. The amount of total light gas (recycled gas) circulated to the reaction system per 1 part by mass of the hydrocarbon supplying raw material is preferably 0.1 to 10 parts by mass and preferably 0.5 to 3 parts by mass.

[(z1-2) Gas-Liquid Separation Step of Reaction Bed Effluent]

In this step, the effluent 3 from the conversion reaction step (z1-1) is introduced into a gas-liquid separation zone composed of one or more gas-liquid separators 4, and gas-liquid separation is carried out under relatively high pressure to separate the effluent 3 into a liquid component (high-pressure separation liquid) containing an aromatic hydrocarbon as the main component and a light gas (high-pressure separation gas) such as hydrogen, methane, ethane, propane, and butane. As the separation conditions, the temperature is generally 10° C. to 50° C. and preferably 20° C. to 40° C., and the pressure is generally 0.5 to 8 MPa and preferably 1 to 3 MPa.

The reaction bed effluent is cooled to 30° C. to 50° C. by indirect heat exchange with a low-temperature raw material hydrocarbon or the like before being introduced into this gas-liquid separation step, and as necessary, a part of the light gas can be separated to reduce the load of the process of separating hydrogen from the gas-liquid separation step and the light gas. For example, the cooled reaction bed effluent can be subjected to gas-liquid separation at a low pressure of 0.2 to 0.35 MPa using a low-pressure gas-liquid separator before being introduced into the gas-liquid separation step. Next, the column top gas of the low-pressure gas-liquid separator, the pressure of which has been raised 1 to 3 MPa by carrying out two or three repetitions of compression, cooling, and gas-liquid separation, and the column bottom liquid of the low pressure gas-liquid separator, which has been pressurized by a pump are allowed to join with each other and subsequently can be introduced into the gas-liquid separation step. Further, it is also possible to carry out introduction into the gas-liquid separation step after a condensate generated when the column top gas is compressed and the column bottom liquid are allowed to join with each other without allowing the column top gas and the column bottom liquid to join with each other.

[(z1-3) Step of Separating Hydrogen from Separation Gas]

In this step, hydrogen is selectively separated from the high-pressure separation gas separated in the gas-liquid separation step (z1-2), and a recycled gas containing methane and/or ethane is obtained. As the hydrogen separation method for this case, a conventionally known method such as a membrane separation method or a cryogenic separation method is used. The membrane separation method is preferable from the viewpoint of the efficiency of selective separation of hydrogen, but in a case where off-gas from the cryogenic separation method is used as a recycled gas, the unreacted propane can be reacted to the maximum as compared with the off-gas from the membrane separation method, which provides an advantage that the yield of the aromatic hydrocarbon can be increased by 1% to 3% by mass. Which method to use is determined from an economic point of view. As the membrane separation device, for example, a separation membrane using polyimide, polysulfone, or a blending product of polysulfone and polydimethylsiloxane is commercially available. A part of the recycled gas obtained in this step is discharged to the outside of the system in order to keep the total circulating gas amount within a certain range. In order to recover high-purity hydrogen, a membrane separation device or adsorption/desorption separation device (PSA) as a recovery system is preferably installed at the rear part of the membrane separation device. The choice of device in the rear part is decided from an economic point of view.

[(z1-4) Step of Separating Aromatic Hydrocarbon from Separation Liquid]

In this step, an aromatic hydrocarbon and a low boiling point hydrocarbon gas are separated from the high-pressure separation liquid obtained in the gas-liquid separation step (z1-2), and a stabilizer (distillation column) is used as the separation device. The low boiling point hydrocarbon gas separated as the column top fraction is composed of C3 to C4 hydrocarbons and may be used as a recycled gas.

Since the column bottom fraction contains a BTX fraction and a heavy fraction having 9 or more carbon atoms, BTX is further separated and purified. For example, each of benzene, toluene, and xylene is recovered by distillation and then purified with a solvent such as sulfolane depending on the required product purity.

[(z1-5) Xylene Conversion Step of Subjecting Toluene to Disproportionation Reaction]

In this step, toluene in the BTX separated and recovered in the step (z1-4) is subjected to a disproportionation reaction with the disproportionation reaction device 5 and converted to xylene.

The reaction conditions for the disproportionation reaction are not particularly limited as long as xylene can be obtained.

It is desirable to carry out the disproportionation reaction by bringing the toluene separated and recovered in the step (z1-4) into contact with a catalyst, where the toluene is supplied preferably at a liquid hourly space velocity (LHSV) of $0.01\ h^{-1}$ or more and more preferably $0.1\ h^{-1}$ or more, and preferably $20\ h^{-1}$ or less and more preferably $10\ h^{-1}$ or less.

In the disproportionation reaction, the reaction temperature is preferably 200° C. or higher, more preferably 230° C. or higher, still more preferably 260° C. or higher, and preferably 550° C. or lower, more preferably 530° C. or lower, and particularly preferably 510° C. or lower.

In a case where the reaction temperature is lower than the lower limit value of the above range, the activation of the aromatic hydrocarbon is insufficient, and the conversion rate of the aromatic hydrocarbon tends to decrease. On the other hand, in a case where the reaction temperature exceeds the upper limit value of the above range, energy consumption is excessive and the catalyst life tends to be shortened.

In the disproportionation reaction, the reaction pressure is preferably equal to or higher than the atmospheric pressure, more preferably 0.1 MPaG or higher, still more preferably 0.5 MPaG or higher, and preferably 10 MPaG or lower and more preferably 5 MPaG or lower.

Further, in a case where the disproportionation reaction is carried out, an inert gas such as nitrogen gas or helium gas or hydrogen gas for suppressing coking may be allowed to flow or pressurized in the reaction system.

The reaction catalyst that is used for the disproportionation reaction is not particularly limited as long as it is an aromatic conversion catalyst and causes the disproportionation reaction.

The reaction catalyst is preferably a catalyst that can selectively dealkylate an ethyl group and a propyl group while retaining a methyl group and at the same time has a transalkylating ability.

Specifically, the reaction catalyst is preferably a shape-selective metallosilicate catalyst, more preferably a crystalline aluminosilicate, and still more preferably a zeolite.

As the zeolite, any zeolite selected from mordenite, a Y zeolite, an X zeolite, a beta zeolite, a ZSM-5, and the like can be used; however, ZSM-5 is preferable.

In the first embodiment, in the xylene conversion step, two molecules of toluene can be converted to obtain one molecule of benzene and one molecule of xylene by the disproportionation reaction.

According to the first embodiment, in the process of producing an aromatic hydrocarbon using a hydrocarbon having 2 to 7 carbon atoms as the main raw material, it is possible to selectively produce benzene or xylene having a high added value from cheap toluene. As a result, the profitability of the entire process can be improved.

The unreacted substance (toluene) in the step (z1-5) can be further circulated in the gas-liquid separator 4 to further increase the xylene yield.

[(z1-6) Step of Mixing Raw Material Light Hydrocarbon with Recycled Gas]

This step is an optional step in which a raw material light hydrocarbon is mixed with the recycled gas containing methane and/or ethane, which is obtained in the hydrogen gas separation step and the low boiling point hydrocarbon gas separated in the aromatic hydrocarbon separation step, and the mixing can be carried out in the pipe. This mixture is introduced into the conversion reaction step. The mixing rate of the recycled gas and the low boiling point hydrocarbon gas per 1 part by mass of the raw material light hydrocarbon is 0.1 to 10 parts by mass and preferably 0.5 to 3 parts by mass. In a case where methane and/or ethane is used as a recycled gas in this manner, the following effects can be obtained. That is, the aromatization reaction by cyclodehydrogenation is an endothermic reaction, which lowers the catalyst layer temperature and is disadvantageous to the aromatization reaction. Methane and/or ethane does not become aromatic under this reaction conditions and thus is regarded as an inert gas. In a case of being heated, methane and/or ethane acts as a heat supplying medium, suppresses the temperature decrease at the catalyst layer, advantageously promotes the aromatization reaction, and can improve the yield of the aromatic hydrocarbon. In addition, the partial pressure of hydrogen produced in the conversion reaction of the raw material can be reduced by recycling, the aromatization reaction can be promoted advantageously, and as a result, the yield of the aromatic hydrocarbon can be improved. Further, since the speed of gas in the reaction layer is increased (GHSV is increased), the contact time between the reaction substrate and the catalytic active site is shortened, and the excessive reaction that gives a coke-like substance can be suppressed.

As a result, the decrease in activity that occurs as the reaction time passes can be suppressed, and the yield of the aromatic hydrocarbon can be maintained at a high level. In commercial devices, the recycling gas ratio is determined from an economic point of view.

<Crystalline Aluminosilicate-Containing Catalyst (Z)>

The catalyst (Z) used in the present embodiment contains a crystalline aluminosilicate.

(Crystalline Aluminosilicate)

The structure of the crystalline aluminosilicate contained in the catalyst (Z) is not particularly limited; however, a pentasil type zeolite is preferable. Among them, a zeolite having an MFI type and/or MEL type crystal structure is more preferable (the crystalline aluminosilicate having a three-dimensionally linked structure is referred to as the zeolite). The MFI type and MEL type zeolites belong to the conventionally known zeolite structure types published by "The Structure Commission of the International Zeolite Association" (Atlas of Zeolite Structure Types, W. M. Meiyer and D. H. Olson (1978). Distributed by Polycrystal Book Service, Pittsburgh, Pa., USA). An example of the MFI type zeolite is ZSM-5, and an example of the MEL type zeolite is ZSM-11.

The crystalline aluminosilicate contained in the catalyst (Z), a crystalline aluminosilicate in which gallium or zinc is present, a crystalline aluminosilicate on which gallium or zinc is supported (hereinafter referred to as a "gallium-supporting crystalline aluminosilicate" or a "zinc-supporting crystalline aluminosilicate"), or a crystalline aluminosilicate in which gallium or zinc is present and on which gallium or zinc is supported can be used. However, a crystalline aluminosilicate containing gallium or zinc at least therein is preferable. Further, a crystalline aluminosilicate containing a gallium cation or a zinc cation therein is more preferable.

From the viewpoint of the yield of the monocyclic aromatic hydrocarbon having 6 to 8 carbon atoms, the crystalline aluminosilicate contained in the catalyst (Z) particularly preferably contains gallium.

The crystalline aluminosilicate contained in the catalyst (Z) is preferably produced by inserting gallium or zinc into a crystalline aluminosilicate by an ion exchange method. Examples of the ion exchange method include a method in which a gallium source or zinc source is used in the form of a solution (in many cases, an aqueous solution) and a crystalline aluminosilicate is immersed in the solution or a method in which a crystalline aluminosilicate and a gallium source or a zinc source are physically mixed in a solid state to carry out ion exchange.

In this case, as the gallium source, a gallium salt such as gallium nitrate or gallium chloride, gallium oxide, or the like can be preferably used. In the case of a water-reactive material such as gallium chloride or solid gallium oxide, a method in which a crystalline aluminosilicate and a gallium source are physically mixed in a solid state to carry out ion exchange is preferable. Similarly, as the zinc source, zinc nitrate, zinc chloride, or zinc oxide can be preferably used. Further, in a case of carrying outing ion exchange, a method of heating in an atmosphere of a reducing gas, an inert gas, or a mixed gas containing them is preferable.

The particle size of the crystalline aluminosilicate contained in the catalyst (Z) is preferably 0.05 to 20 μm, more preferably 0.1 to 10 μm, particularly preferably 0.5 to 5 μm, and extremely preferably 1 to 3 μm.

Further, the content of particles having the above particle size is preferably 80% by mass or more based on the mass of all particles.

In a case where the size of the reaction molecule and the pore size of the crystalline aluminosilicate are substantially the same, the diffusion rate of the molecule tends to be low in the crystalline aluminosilicate pores. Accordingly, in a case where the particle size is 20 μm or less, the reaction molecule easily approaches the active site in the deep portion of the pore, and thus the active site is easily used effectively during the reaction.

In a case where the crystalline aluminosilicate is obtained by hydrothermal synthesis, examples of the factor that affects the size of the produced particle include the kind of silica source, the amount of an organic additive such as a quaternary ammonium salt, the amount or kind of an inorganic salt as a mineralizing agent, the base quantity in a gel, the pH of a gel and the temperature raising rate during the crystallization operation, the temperature, and the stirring rate. In a case where these conditions are appropriately adjusted, a crystalline aluminosilicate having a particle size in the above range can be obtained.

In the present invention, the silica/alumina ratio (the molar ratio of silicon to aluminum) of the crystalline alumina silicate is preferably 10 or more and 1,000 or less and more preferably 35 or more and 100 or less.

In the present invention, the content of gallium with respect to 100 parts by mass of the catalyst (Z) is preferably 0.1 part by mass or more and 10.0 parts by mass or less, more preferably 1.0 part by mass or more and 7.0 parts by mass or less, and still more preferably 2.0 parts by mass or more and 5.0 parts by mass or less.

The molar ratio of gallium to aluminum (atomic ratio, Ga/Al) is preferably 0.1 or more and 10.0 or less, more preferably 0.5 or more and 7.0 or less, and particularly preferably 1.0 or more and 5.0 or less.

The crystalline aluminosilicate contained in the catalyst (Z) can be subjected, as desired, to various activation treatments, which are generally performed in a case where a crystalline aluminosilicate is used as a catalyst component. That is, the crystalline aluminosilicate contained in the catalyst (Z) includes not only those produced by the method such as the hydrothermal synthesis but also those obtained by the modification treatment or activation treatment thereof.

For example, after performing ion exchange of the crystalline aluminosilicate in an aqueous solution containing an ammonium salt such as ammonium chloride, ammonium fluoride, ammonium nitrate, or ammonium hydroxide to form an ammonium type crystalline aluminosilicate, it is possible to introduce a desired metal other than the alkali metal or the alkaline earth metal by performing ion exchange in an aqueous solution containing a metal ion other than the alkali metal ion or the alkaline earth metal ion or impregnating the aqueous solution.

Further, in a case of being heated in air, or in a nitrogen or hydrogen atmosphere at a temperature of 200° C. to 800° C. and preferably at a temperature of 350° C. to 700° C., for 3 to 24 hours to remove ammonia, the ammonium type crystalline aluminosilicate can be activated to have an acid type structure. In addition, the acid type catalyst may be treated with hydrogen or a mixed gas of hydrogen and nitrogen under the above conditions. Further, the acid type catalyst may be subjected to ammonia modification in which the acid type catalyst is brought into contact with ammonia under dry conditions. Generally, it is preferable that the catalyst (Z) is used after being subjected to the above-described activation treatment before being brought into contact with the hydrocarbon raw material.

The active component of the catalyst (Z) is the crystalline aluminosilicate; however, the catalyst (Z) may contain a carrier, a molding aid, or the like for the purpose of facilitating molding or improving the mechanical strength of the catalyst.

In a case where a carrier, a molding aid, or the like is contained, the content of the crystalline aluminosilicate occupied in the total mass of the catalyst (Z) is not particularly limited; however, the crystalline aluminosilicate is preferably 40% to 95% by mass, more preferably 50% to 90% by mass, and still more preferably 60% to 80% by mass, with respect to the total mass of the catalyst (Z).

The catalyst (Z) containing crystalline aluminosilicate is formed into various molded bodies having a shape such as a granule shape, a sphere shape, a plate shape, or a pellet shape by extrusion molding, spray drying, tableting molding, rolling granulation, in-oil granulation, or the like. Further, at the time of molding, it is desirable to use an organic compound type lubricant in order to improve the moldability.

In general, a composition of a crystalline aluminosilicate can be molded before being subjected to the ion exchange step for the crystalline aluminosilicate by using ammonium ions or the like, or the crystalline aluminosilicate can be molded after being subjected to the ion exchange.

Further, in the present embodiment, the catalyst (Z) may contain an additive in addition to the above-described crystalline aluminosilicate.

The additive is not particularly limited, and examples thereof include an inorganic oxide such as alumina boria, silica, silica alumina, or aluminum phosphate, a clay mineral such as kaolin or montmorillonite, and an inorganic phosphorus compound, and an organic phosphorus compound. The amount of the additive to be added is not particularly limited; however, the additive is added in the catalyst composition so that the content thereof is 50% by mass or less, more preferably 30% by mass or less, and still more preferably 15% by mass or less.

Further, a metal component as an auxiliary component can be supported in the catalyst (Z) and used. The metal component as an auxiliary component may be supported on a crystalline aluminosilicate, may be supported on other additives or may be supported on a crystalline aluminosilicate and other additives.

Examples of such an auxiliary metal component include a metal having a dehydrogenating ability and a metal having an effect of suppressing carbon precipitation. Specific examples of the auxiliary metal component as a component improving catalytic activity include magnesium, calcium, strontium, barium, lantern, cerium, praseodymium, neodymium, samarium, europium, gadolinium, terbium, dysprosium, holmium, erbium, thulium, ytterbium, lutetium, titanium, vanadium, chromium, molybdenum, tungsten, manganese, rhenium, iron, ruthenium, cobalt, rhodium, iridium, nickel, palladium, platinum, copper, silver, zinc, aluminum, indium, germanium, tin, lead, phosphorus, antimony, bismuth, and selenium. These metals can be used alone or in a combination of two or more thereof, and the amount of the supported metal is 0.1% to 10% by mass in terms of metal. As the metal supporting method, conventionally known techniques such as an ion exchange method, an impregnation method, and physical mixing can be used. Further, when the pentasil type zeolite is synthesized, an auxiliary component metal can be incorporated by adding the above-described metal component as an auxiliary component. In addition, as the auxiliary metal component that has the effect of suppressing the accumulation of coke during the reaction, one or more kinds of metals selected from magnesium, calcium, lantern, cerium, praseodymium, neodymium, samarium, europium, gadolinium, terbium, dysprosium, holmium, erbium, thulium, ytterbium, lutetium, ruthenium, and iridium can be supported, and the amount of the supported metal is 0.01% to 5% by mass in terms of metal.

<Raw Material Containing a Light Hydrocarbon Having 2 to 7 Carbon Atoms as the Main Component>

The raw material used in the present embodiment contains a light hydrocarbon having 2 to 7 carbon atoms, and the content of the light hydrocarbon having 2 to 7 carbon atoms in the raw material is not particularly limited; however, it is preferably 20% by mass or more, more preferably 40% by mass or more, and particularly preferably 60% to 100% by mass.

The light hydrocarbon having 2 to 7 carbon atoms is not particularly limited; however, it may be linear, branched, or cyclic, and it may be paraffin or olefin. In addition, a mixture of thereof may be used. Specific examples of such hydrocarbons include linear saturated aliphatic hydrocarbons having 2 to 7 carbon atoms (ethane, propane, normal butane, normal pentane, normal hexane, and normal heptane), branched saturated aliphatic hydrocarbons (isobutane, 2-methylbutane, 2,2-dimethylbutane, 2-methylpentane, 3-methylpentane, 2,3-dimethylbutane, 2-methylhexane, 3-methylhexane, 2, 2-dimethylpentane, 2,3-dimethylpentane, 2,4-dimethylpentane, and 2,2,3-trimethylbutane), cyclic saturated aliphatic hydrocarbons (cyclopropane, cyclobutane, cyclopentane, 1-methylcyclopentane, 1,1-dimethylcyclopentane, 1,2-dimethylcyclopentane, 1,3-dimethylcyclopentane, cyclohexane, and methylcyclohexane), linear unsaturated aliphatic hydrocarbons (ethylene, propylene, normal butene, normal pentene, normal hexene, and normal heptene), branched unsaturated aliphatic hydrocarbons (isobutene, 2-methylbutene, 2-methylpentene, 3-methylpentene, 2-methylhexene, and 3-methylhexene), cyclic unsaturated aliphatic hydrocarbons (cyclopentene, methylcyclopentene, cyclohexene, and methylcyclohexene), a liquefied petroleum gas containing propane and butane as main components, a light fraction (light naphtha) in naphtha fraction, which has a boiling point of 100° C. or less and contains paraffin having 5 to 7 carbon atoms as the main component, a C4 fraction from a fluid catalytic cracker (FCC), and raffinate of an ethylene cracker.

Second Embodiment

Figure 2:
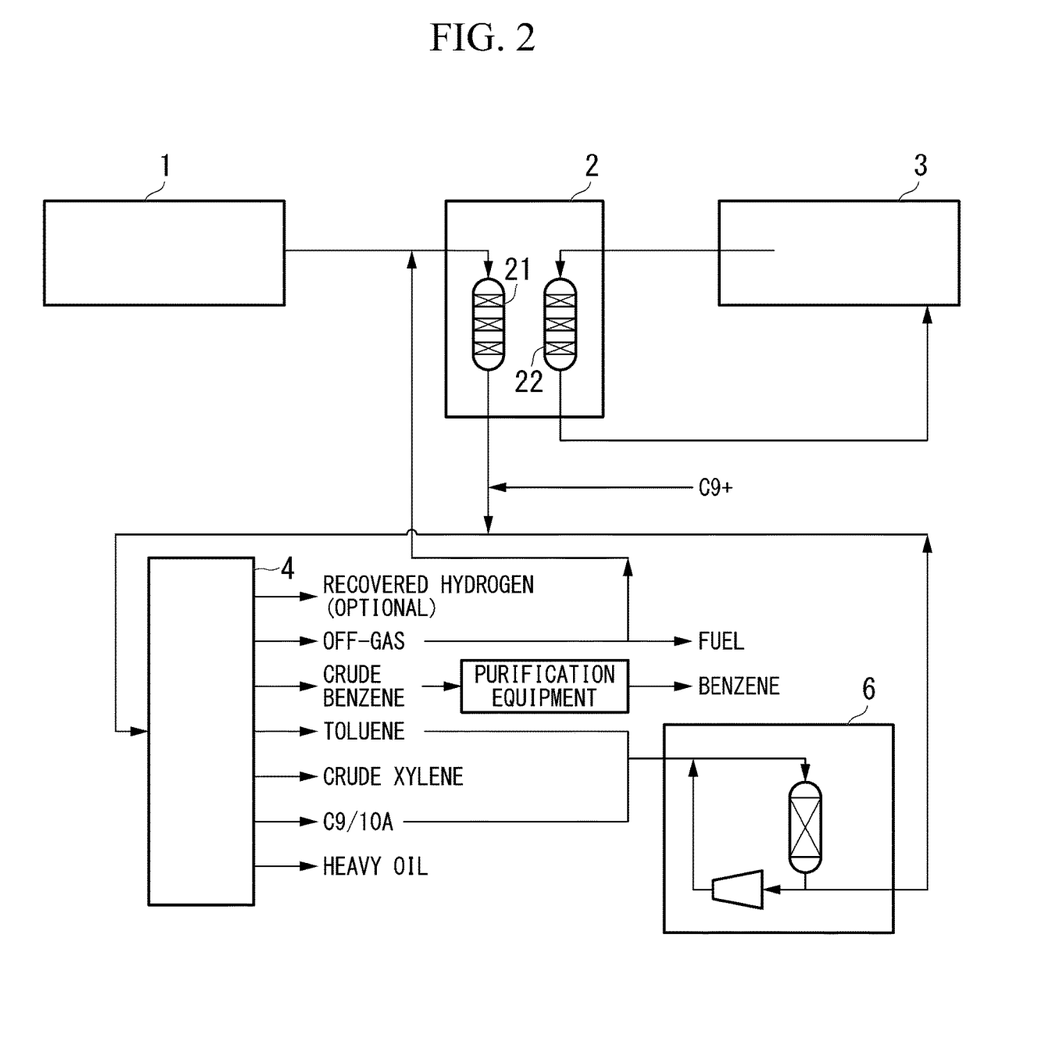
FIG. 2 a diagram for explaining a second embodiment of the method for producing xylene of the present invention.

As shown in FIG. 2, in the second embodiment of the method for producing xylene of the present invention (hereinafter, may be simply referred to as the "second embodiment"), a raw material 1 containing a light hydrocarbon having 2 to 7 carbon atoms as the main component is brought into contact with a catalyst (Z) in a conversion reaction device 2, and then a product containing a monocyclic aromatic hydrocarbon having 6 to 8 carbon atoms is produced. Subsequently, the product is subjected to a transalkylation reaction in the transalkylation reaction device 6 to, thereby xylene being produced.

Specifically, it is preferable that the second embodiment mainly has the following five steps (z2-1) to (z2-5). In addition to the following five steps (z2-1) to (z2-5), the method for producing a monocyclic aromatic hydrocarbon of the present invention may have a step (z2-6).

(z2-1) Conversion reaction step
(z2-2) Gas-liquid separation step of reaction bed effluent
(z2-3) Step of separating hydrogen from separation gas
(z2-4) Step of separating aromatic hydrocarbon from separation liquid
(z2-5) Xylene conversion step of subjecting aromatic hydrocarbon to transalkylation reaction (z2-6) Step of mixing raw material light hydrocarbon with recycled gas In the second embodiment, the steps (z2-1) to (z2-4) and (z2-6) are the same as the steps (z1-1) to (z1-4) and (z2-6) in the first embodiment.

In the second embodiment, a heavy fraction having 9 or more carbon atoms may be mixed with the reaction bed effluent to be subjected to the step (z2-2). In a case where the heavy fraction having 9 or more carbon atoms is mixed with the reaction bed effluent to be subjected to the step (z2-2), the yield of xylene can be increased in the step (z2-5), and the profitability of the entire process can be improved by converting the above heavy fraction having 9 or more carbon atoms to xylene having a high added value.

[(z2-5) Xylene Conversion Step of Subjecting Aromatic Hydrocarbon to Transalkylation Reaction]

In this step, the toluene separated and recovered in the step (z2-4) and the heavy fraction having 9 or more carbon atoms are subjected to a transalkylation reaction in the transalkylation reaction device 6 to be converted into xylene.

The reaction conditions for the transalkylation reaction are not particularly limited as long as xylene can be obtained.

It is desirable to carry out the transalkylation reaction by bringing the toluene separated and recovered in the step (z2-4) and the heavy fraction having 9 or more carbon atoms into contact with a catalyst, where the toluene and the heavy fraction are supplied preferably at a liquid hourly space velocity (LHSV) of 0.5 $h^{-1}$ or more and 4.0 $h^{-1}$ or less and more preferably 1.0 $h^{-1}$ or more and 3.0 $h^{-1}$ or less.

In the transalkylation reaction, the reaction temperature is preferably 300° C. or higher and more preferably 350° C. or higher, and preferably 500° C. or lower and more preferably 450° C. or lower.

In a case where the reaction temperature is equal to or higher than the lower limit value of the above range, the reaction rate is sufficiently high and the xylene yield increases. On the other hand, in a case where the reaction temperature is equal to or lower than the upper limit value of the above range, the production of xylene is advantageous in terms of equilibrium.

In the transalkylation reaction, the reaction pressure is preferably 2.0 MPaG or higher and more preferably 2.5 MPaG or higher, and preferably 7.0 MPaG or lower and more preferably 5.0 MPaG or lower.

In a case where the reaction pressure is equal to or higher than the lower limit value of the above range, the decrease in hydrogen partial pressure is suppressed and the catalyst deterioration due to coke precipitation can be prevented. On the other hand, in a case where the reaction pressure is equal to or higher than the upper limit value of the above range, the construction cost of the device can be reduced from the viewpoint of the pressure resistance of the material of the reactor.

The reaction catalyst that is used in the transalkylation reaction is not particularly limited as long as it is an aromatic conversion catalyst and causes a disproportionation reaction.

The reaction catalyst is preferably a catalyst that can selectively dealkylate an ethyl group and a propyl group while retaining a methyl group and at the same time has a transalkylating ability.

Specifically, the reaction catalyst is preferably a shape-selective metallosilicate catalyst, more preferably a crystalline aluminosilicate, and still more preferably a zeolite.

As the zeolite, any zeolite selected from mordenite, Y zeolite, X zeolite, beta zeolite, ZSM-5 and the like can be used; however, mordenite and/or beta zeolite is preferable.

In the second embodiment, in the xylene conversion step, two molecules of aromatic hydrocarbons having a different number of carbon atoms can be converted to obtain two molecules of xylene by the transalkylation reaction.

Specifically, one molecule of toluene and one molecule of trimethylbenzene can be converted to obtain two molecules of xylene.

According to the second embodiment, in the process of producing an aromatic hydrocarbon using a hydrocarbon having 2 to 7 carbon atoms as the main raw material, it is possible to selectively produce xylene having a high added value from cheap toluene and the heavy fraction having 9 or more carbon atoms. As a result, the profitability of the entire process can be improved.

Third Embodiment

Figure 3:
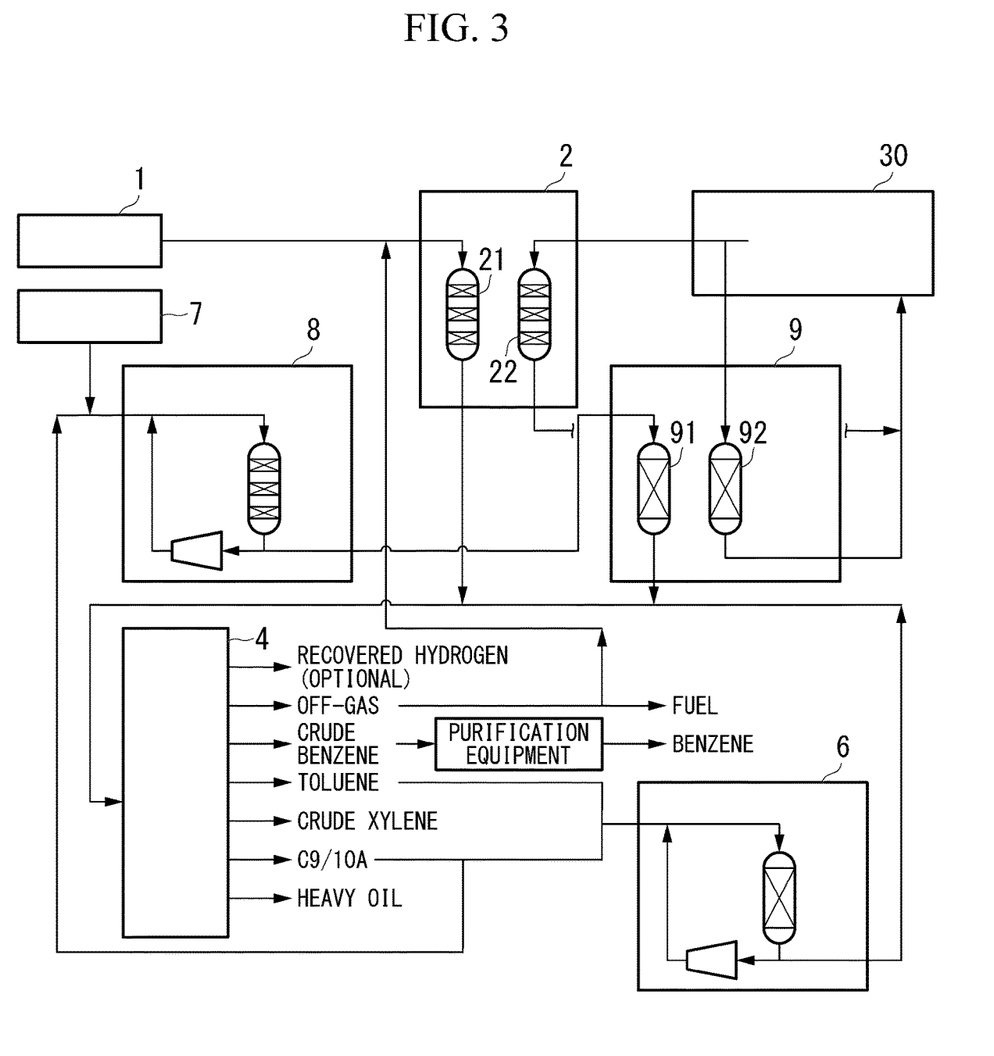
FIG. 3 a diagram for explaining a third embodiment of the method for producing xylene of the present invention.

As shown in FIG. 3, in the third embodiment of the method for producing xylene of the present invention (hereinafter, may be simply referred to as the "third embodiment"), a raw material 1 containing a light hydrocarbon having 2 to 7 carbon atoms as the main component is brought into contact with a catalyst (Z) in a conversion reaction device 2, and then a product containing a monocyclic aromatic hydrocarbon having 6 to 8 carbon atoms is produced. Further, a raw material derived from a raw material oil 7 having a 10% by volume distilling temperature of 140° C. or higher and a 90% by volume distilling temperature of 380° C. or lower is brought into contact with a crystalline aluminosilicate-containing catalyst (F) (hereinafter, may be simply referred to as a "catalyst (F)" to produce the product containing a monocyclic aromatic hydrocarbon having 6 to 8 carbon atoms. Subsequently, the product is subjected to a transalkylation reaction in the transalkylation reaction device 6 to, thereby xylene being produced.

Specifically, it is preferable that the third embodiment mainly has the following seven steps (z3-1), (f3-1), (f3-2), and (z3-2) to (z3-5). Further, the third embodiment may include a step (z3-6), in addition to the above seven steps.

(z3-1) Conversion reaction step
(f3-1) Hydrogenation step
(f3-2) Cracking and reforming step
(z3-2) Gas-liquid separation step of reaction bed effluent
(z3-3) Step of separating hydrogen from separation gas
(z3-4) Step of separating aromatic hydrocarbon from separation liquid
(z3-5) Xylene conversion step of subjecting aromatic hydrocarbon to transalkylation reaction (z3-6) Step of mixing raw material light hydrocarbon with recycled gas In the third embodiment, the steps (z3-1) to (z3-6) are the same as the steps (z1-1) to (z1-6) in the first embodiment.

[(f3-1) Hydrogenation Step]

In this step, the raw material oil 7 having a 10% by volume distilling temperature of 140° C. or higher and a 90% by volume distilling temperature of 380° C. or lower is hydrogenated in the hydrogenation device 8.

In a case where an oil having a 10% by volume distilling temperature of lower than 140° C. is used, the monocyclic aromatic hydrocarbon is produced from the light oil, which does not meet the gist of the present invention of selectively producing a large amount of xylene. Further, in a case where an oil having a 90% by volume distilling temperature exceeding 380° C. is used, the yield of the monocyclic aromatic hydrocarbon is low, and the amount of the coke accumulated on the catalyst for producing a monocyclic aromatic hydrocarbon increases, which easily causes a drastic decrease in catalytic activity.

The 10% by volume distilling temperature of the raw material oil is preferably 150° C. or higher, and the 90% by volume distilling temperature of the raw material oil is preferably 360° C. or lower.

The 10% by volume distilling temperature and the 90% by volume distilling temperature referred to here mean values measured in accordance with JIS K2254 "Petroleum products—Distillation test method".

Examples of the raw material oil having a 10% by volume distilling temperature of 140° C. or higher and a 90% by volume distilling temperature of 380° C. or lower include LCO, a hydrogenated and refined oil of LCO, a coal liquefied oil, a hydrocracked and refined oil of heavy oil, straight-run kerosene, straight-run light oil, coker kerosene, coker light oil, and a hydrocracked refined oil of oil sand.

More specifically, in the step (f3-1), for example, a bicyclic aromatic hydrocarbon contained in light cycle oil (hereinafter referred to as "LCO") which is a cracked light oil produced by a fluid catalytic cracker (hereinafter, referred to as "FCC") a thermally cracked heavy oil obtained from an ethylene production device, or the like is selectively hydrogenated and converted into a monocyclic aromatic hydrocarbon (naphthenobenzenes or the like) having only one hydrogenated aromatic ring. Here, examples of the monocyclic aromatic hydrocarbon include indane, tetralin, and alkylbenzene.

As a raw material oil, the heavy fraction having 9 or more carbon atoms recovered in the step (z3-4) can also be used.

In a case where the hydrogenation treatment is partially carried out in this manner, the amount of hydrogen consumed in the hydrogenation reaction step can be reduced, and at the same time, the amount of heat generated during the treatment can be reduced. For example, in a case where naphthalene, which is a representative example of a bicyclic aromatic hydrocarbon, is hydrogenated to decalin, the amount of hydrogen consumed per mol of naphthalene is 5 mol; however, in a case of being hydrogenated to tetralin, the amount of hydrogen consumed is 2 mol, which is feasible for hydrogenation. Further, in the case of a fraction containing an indene skeleton in the raw material oil, even the indane skeleton may be hydrogenated.

As the hydrogen that is used in this hydrogenation step (hydrogenation treatment), hydrogen produced in the cracking and reforming reaction step (f3-2) can also be used.

Such a hydrogenation step (hydrogenation reaction step) can be carried out in a conventionally known hydrogenation reactor. In this hydrogenation treatment, the hydrogen partial pressure at the inlet of the reactor is preferably 1 to 9 MPa. The lower limit is more preferably 1.2 MPa or higher and still more preferably 1.5 MPa or higher. In addition, the upper limit is more preferably 7 MPa or lower and still more preferably 5 MPa or lower.

In a case where the hydrogen partial pressure is equal to or higher than the lower limit value of the above range, coke formation on the catalyst can be suppressed, and thus the catalyst life can be extended. On the other hand, in a case where the hydrogen partial pressure is equal to or lower than the upper limit value of the above range, the amount of hydrogen consumed can be reduced and the construction cost of the reactor, peripheral equipment, and the like can be reduced.

Further, the liquid hourly space velocity (LHSV) in the hydrogenation treatment is preferably 0.05 to 10 $h^{-1}$. The lower limit is more preferably 0.1 $h^{-1}$ or more and still more preferably 0.2 $h^{-1}$ or more. In addition the upper limit is more preferably 5 $h^{-1}$ or less and still more preferably 3 $h^{-1}$ or less. In a case where the LHSV is less than 0.05 $h^{-1}$, the construction cost of the reactor may increase. On the other hand, in a case where the LHSV exceeds 10 $h^{-1}$, the hydrogenation treatment of the raw material oil is not sufficiently achieved, and there is a concern that the reactivity in the cracking and reforming reaction in the subsequent stage may decrease.

The treatment temperature (the hydrogenation reaction temperature) in the hydrogenation treatment is preferably 150° C. to 400° C. The lower limit is more preferably 170° C. or higher and still more preferably 190° C. or higher.

In addition, the upper limit is more preferably 380° C. or lower and still more preferably 370° C. or lower. In a case where the reaction temperature is lower than 150° C., the hydrogenation treatment of the raw material oil tends to be insufficiently achieved. On the other hand, in a case where the reaction temperature exceeds 400° C., the production of gas as a by-product increases, and the yield of the hydrogenation-treated oil decreases, which is not desirable.

The rate of hydrogen to oil in the hydrogenation treatment is preferably 100 to 2,000 NL/L.

The lower limit is more preferably 110 NL/L or more and still more preferably 120 NL/L or more. Further, the upper limit is more preferably 1,800 NL/L or less and still more preferably 1,500 NL/L or less. In a case where the rate of hydrogen to oil is less than 100 NL/L, coke formation on the catalyst at the outlet of the reactor proceeds, and the catalyst life tends to be shortened. On the other hand, in a case where the rate of hydrogen to oil exceeds 2,000 NL/L, the construction cost of the recycling compressor may increase.

Although the reaction type in the hydrogenation treatment is not particularly limited, it can typically be selected from various processes such as a fixed bed type and a moving bed type, and a fixed bed type is preferable because the construction cost and the operating cost are low. Further, the hydrogenation reaction device is preferably a tower-shaped device.

The catalyst for hydrogenation treatment that is used in the hydrogenation treatment is not particularly limited, and various catalysts can be used as long as they are capable of selectively hydrogenating a bicyclic aromatic hydrocarbon contained in raw material oil and converting it into a monocyclic aromatic hydrocarbon (naphthenobenzenes or the like) having only one hydrogenated aromatic ring. Examples of the preferred catalyst for hydrogenation treatment include a catalyst containing at least one metal selected from metals of Group 6 of the periodic table and at least one metal selected from metals of Groups 8 to 10 of the periodic table. The metal of Group 6 of the periodic table is preferably molybdenum, tungsten, or chromium and particularly preferably molybdenum or tungsten. The metal of Groups 8 to 10 of the periodic table is preferably iron, cobalt, or nickel and more preferably cobalt or nickel. Each of these metals may be used alone, or two or more kinds thereof may be used in combination. As specific examples of the metal combination, molybdenum-cobalt, molybdenum-nickel, tungsten-nickel, molybdenum-cobalt-nickel, tungsten-cobalt-nickel, or the like is preferably used. Here, the periodic table refers to a long-periodic table defined by the International Union of Pure and Applied Chemistry (IUPAC).

The catalyst for hydrogenation treatment is preferably one in which the metal is supported on an inorganic carrier containing aluminum oxide. Preferred examples of the inorganic carrier containing an aluminum oxide include alumina, alumina-silica, alumina-boria, alumina-titania, alumina-zirconia, alumina-magnesia, alumina-silica-zirconia, alumina-silica-titania, and a carrier obtained by adding, to alumina, porous inorganic compounds such as various clay minerals such as zeolite, sepiolite, and montmorillonite. Among them, alumina is particularly preferable.

The catalyst for hydrogenation treatment is preferably a catalyst obtained by supporting 10% to 30% by mass of at least one metal selected from metals of Group 6 of the periodic table and 1% to 7% by mass of at least one metal selected from metals of Groups 8 to 10 of the periodic table on the inorganic carrier containing an aluminum oxide, based on the total mass of the catalyst, which is the total mass of the inorganic carrier and the metal. In a case where the amount of the supported metal of Group 6 of the periodic table and the amount of the supported metal of Groups 8 to 10 of the periodic table are less than each of the lower limits the catalyst tends not to exhibit sufficient hydrogenation treatment activity. On the other hand, in a case where the amounts of the supported metals exceed each of the upper limits, the catalyst cost increases, the aggregation of the supported metal or the like easily occurs, and thus the catalyst tends to not exhibit sufficient hydrogenation treatment activity.

The precursor of the metal species that is used in a case of supporting the metal on the inorganic carrier is not particularly limited; however an inorganic salt of the metal, an organometallic compound, or the like is used, and a water-soluble inorganic salt is preferably used. In the supporting step, a solution of this metal precursor, preferably an aqueous solution of this metal precursor, is used for the supporting. As the supporting operation, for example, a conventionally known method such as a dipping method, an impregnation method, or a coprecipitation method is preferably adopted.

After drying, the carrier on which the metal precursor is supported is preferably baked in the presence of oxygen, and the metal species is preferably once converted into an oxide. Further, it is preferable that the metal species is made into a sulfide by a sulfurization treatment called pre-sulfurization before carrying out the hydrogenation treatment of the raw material oil.

The conditions for pre-sulfurization are not particularly limited. However, it is preferable that a sulfur compound is added to a petroleum fraction or a thermally cracked heavy oil (hereinafter, referred to as a pre-sulfurized raw material oil), and the resultant mixture is continuously brought into contact with the catalyst for hydrogenation treatment under the following conditions; a temperature of 200° C. to 380° C., an LHSV of 1 to 2 $h^{-1}$, a pressure which identical to the pressure during the hydrogenation treatment operation, and a treatment time of 48 hours or more. The sulfur compound that is added to the pre-sulfurized raw material oil is not limited; however dimethyl disulfide (DMDS), sulfazole, hydrogen sulfide, or the like is preferable, and about 1% by mass of this compound is preferably added with respect to the pre-sulfurized raw material oil based on the mass of the pre-sulfurized raw material oil.

[(F3-2) Cracking and Reforming Reaction Step]

In this step, the hydrogenated oil obtained in the step (f3-1) is brought into contact with a crystalline aluminosilicate-containing catalyst (F) (hereinafter, may be simply referred to as a "catalyst (F)" in a cracking and reforming reaction device 9 to produce a product containing a monocyclic aromatic hydrocarbon having 6 to 8 carbon atoms.

The product obtained in the step (f3-2) is subjected to a gas-liquid separation step (z3-2) together with the reaction bed effluent obtained in the conversion reaction step (z3-1).

(Reaction Type)

Examples of the reaction type in the case where the hydrogenated oil is brought into contact with the catalyst (F) and subjected to the reaction include a fixed bed type, a moving bed type, and a fluidized bed type. In the present embodiment, a fluidized bed type with which the coke component adhered to the catalyst can be continuously removed and the reaction can be stably carried out is preferable, and a fluidized bed type of continuous regeneration, with which the catalyst can continuously circulate between the reactor and the regenerator and reaction and regeneration can be continuously repeated, is particularly preferable. The raw material oil in a case of coming into contact with the catalyst (F) is preferably in a vapor phase state. In addition, the raw material may be diluted with gas as necessary.

As shown in FIG. 3, the catalyst (F) can be regenerated by a regenerator 30. For example, in FIG. 3, the catalyst in the reaction bed 92 is subjected to the regeneration treatment while proceeding with the reaction in the reaction bed 91, but after a lapse of a predetermined period, the reaction bed 91 and the reaction bed 92 can be switched to carry out reaction and regeneration.

(Reaction Temperature)

The reaction temperature in a case where the hydrogenated oil is brought into contact with the catalyst (F) and subjected to the reaction is not particularly limited; however, it is preferably 400° C. to 650° C. In a case where the lower limit of the reaction temperature is 400° C. or higher, the hydrogenated oil can be easily reacted, and the reaction temperature is more preferably 450° C. or higher. Further, in a case where the upper limit of the reaction temperature is 650° C. or lower, the yield of the monocyclic aromatic hydrocarbon can be sufficiently increased, and the reaction temperature is more preferably 600° C. or lower.

(Reaction Pressure)

The reaction pressure in a case where the hydrogenated oil is brought into contact with the catalyst (F) and subjected to the reaction is preferably 1.5 MPaG or lower, and more preferably 1.0 MPaG or lower. In a case where the reaction pressure is 1.5 MPaG or lower, the generation of the by-product of the light gas can be suppressed and the pressure resistance of the reaction device can be lowered.

(Contact Time)

The contact time between the hydrogenated oil and the catalyst (F) is not particularly limited as long as the desired reaction proceeds substantially; however, for example, 1 to 300 seconds are preferable as the passage time of the gas on the catalyst (F). Further, it is more preferable that the lower limit is 5 seconds and the upper limit is 150 seconds. In a case where the contact time is 1 second or more, the reaction can be reliably carried out, and in a case where the contact time is 300 seconds or less, the accumulation of carbonaceous material on the catalyst due to coking or the like can be suppressed. Alternatively, the amount of the light gas generated due to cracking can be suppressed.

(Catalyst (F))

The catalyst (F) used in the step (f3-2) contains a crystalline aluminosilicate.

(Crystalline Aluminosilicate)

The crystalline aluminosilicate is preferably a medium pore zeolite and/or a large pore zeolite since the yield of the monocyclic aromatic hydrocarbon is further increased.

The medium pore zeolite is a zeolite having a 10-membered ring skeleton structure, and examples of the medium pore zeolite include zeolites having the following types of crystal structure; an AEL type, a EUO type, a FER type, an HEU type, an MEL type, an MFI type, an NES type, a TON type, and a WEI type. Among these, an MFI type is preferable because the yield of the monocyclic aromatic hydrocarbon can be further increased.

The large pore zeolite is a zeolite having a 12-membered ring skeleton structure, and examples of the large pore zeolite include zeolites having the following types of crystal structure; an AFI type, an ATO type, a BEA type, a CON type, an FAU type, a GME type, an LTL type, an MOR type, an MTW type, and an OFF type. Among these, a BEA type, an FAU type, or an MOR type is preferable in terms of industrial use, and a BEA type or an MOR type is more preferable because the yield of the monocyclic aromatic hydrocarbon can be further increased.

In addition to the medium pore zeolite and the large pore zeolite, the crystalline aluminosilicate may contain a small pore zeolite having a skeleton structure of a ring having 10 or fewer members and an ultra-large pore zeolite having a skeleton structure of ring having 14 or more members.

Here, examples of the small pore zeolite include zeolites having the following types of crystal structure; an ANA type, a CHA type, an ERI type, a GIS type, a KFI type, an LTA type, an NAT type, a PAU type, and a YUG type.

Examples of the ultra-large pore zeolite include zeolites having the following types of crystal structure; a CLO type and a VPI type.

In a case where the cracking and reforming reaction step is a fixed bed type reaction, the content of the crystalline aluminosilicate in the catalyst for producing a monocyclic aromatic hydrocarbon is preferably 60% to 100% by mass more preferably 70% to 100% by mass, and particularly preferably 90% to 100% by mass, in a case where the total of the catalyst for producing a monocyclic aromatic hydrocarbon is set to 100% by mass. In a case where the content of the crystalline aluminosilicate is 60% by mass or more, the yield of the monocyclic aromatic hydrocarbon can be sufficiently increased.

In a case where the cracking and reforming reaction step is a fluidized bed type reaction, the content of the crystalline aluminosilicate in the catalyst for producing a monocyclic aromatic hydrocarbon is preferably 20% to 60% by mass more preferably 30% to 60% by mass, and particularly preferably 35% to 60% by mass, in a case where the total of the catalyst for producing a monocyclic aromatic hydrocarbon is set to 100% by mass. In a case where the content of the crystalline aluminosilicate is 20% by mass or more, the yield of the monocyclic aromatic hydrocarbon can be sufficiently increased. In a case where the content of the crystalline aluminosilicate exceeds 60% by mass, the content of the binder that can be blended in the catalyst decreases, which is not suitable for the fluidized bed type.

(Gallium and Zinc)

The catalyst for producing a monocyclic aromatic hydrocarbon can contain gallium and/or zinc, as necessary. In a case where gallium and/or zinc is contained, the production rate of the monocyclic aromatic hydrocarbon can be increased.

Examples of the configuration of the containing of gallium in the catalyst for producing a monocyclic aromatic hydrocarbon include a configuration (a crystalline aluminogallosilicate) in which gallium is incorporated in the lattice skeleton of the crystalline aluminosilicate, a configuration (a gallium-supporting crystalline aluminosilicate) in which gallium is supported on the crystalline aluminosilicate, and a configuration including both configurations aforementioned.

Examples of the configuration of the containing of zinc in the catalyst for producing a monocyclic aromatic hydrocarbon include a configuration (a crystalline aluminozincosilicate) in which zinc is incorporated in the lattice skeleton of the crystalline aluminosilicate, a configuration (a zinc-supporting crystalline aluminosilicate) in which zinc is supported on the crystalline aluminosilicate, and a configuration including both configurations aforementioned.

The crystalline aluminogallosilicate and the crystalline aluminozincosilicate have a structure in which structures of $SiO_4$, $AlO_4$, and $GaO_4/ZnO_4$ are present in the skeleton. In addition, the crystalline aluminogallosilicate and the crystalline aluminozincosilicate is obtained by, for example, a method of gel crystallization by hydrothermal synthesis, a method of inserting gallium or zinc into the lattice skeleton of crystalline aluminosilicate, or a method of inserting aluminum into the lattice skeleton of a crystalline gallosilicate or crystalline zincosilicate.

The gallium-supporting crystalline aluminosilicate is a crystalline aluminosilicate obtained by supporting gallium on the crystalline aluminosilicate by a conventionally known method such as an ion exchange method or an impregnation method. In this case, the gallium source is not particularly limited; however, examples thereof include a gallium salt such as gallium nitrate or gallium chloride, and gallium oxide.

The zinc-supporting crystalline aluminosilicate is a crystalline aluminosilicate obtained by supporting zinc on the crystalline aluminosilicate by a conventionally known method such as an ion exchange method or an impregnation method. In this case, the zinc source is not particularly limited; however, examples thereof include a zinc salt such as zinc nitrate or zinc chloride and zinc oxide.

In a case where the catalyst for producing a monocyclic aromatic hydrocarbon contains gallium and/or zinc, the content of gallium and/or zinc in the catalyst for producing a monocyclic aromatic hydrocarbon is preferably 0.01% to 5.0% by mass and more preferably 0.05% to 2.0% by mass, in a case where the total of the catalyst is set to 100% by mass. In a case where the content of gallium and/or zinc is 0.01% by mass or more, the production rate of the monocyclic aromatic hydrocarbon can be increased, and in a case where it is 5.0% by mass or less, the yield of the monocyclic aromatic hydrocarbon can be further increased.

(Phosphorus and Boron)

The catalyst for producing a monocyclic aromatic hydrocarbon preferably contains phosphorus and/or boron. In a case where the catalyst for producing a monocyclic aromatic hydrocarbon contains phosphorus and/or boron, it is possible to prevent a decrease in the yield of the monocyclic aromatic hydrocarbon over time, and it is possible to suppress coke formation on the surface of the catalyst.

Examples of the method for incorporating phosphorus into the catalyst for producing a monocyclic aromatic hydrocarbon include a method of supporting phosphorus on a crystalline aluminosilicate, a crystalline aluminogallosilicate, or a crystalline aluminozincosilicate with an ion exchange method or an impregnation method, a method of incorporating a phosphorus compound at the time of zeolite synthesis to substitute a part of the skeleton of the crystalline aluminosilicate with phosphorus, and a method of using a crystal accelerator containing phosphorus at the time of zeolite synthesis. The phosphate ion-containing aqueous solution used at that time is not particularly limited; however, a solution prepared by dissolving phosphoric acid, diammonium hydrogen phosphate, ammonium dihydrogen phosphate, or other water-soluble phosphate in water at any concentration can be preferably used.

Examples of the method for incorporating boron into the catalyst for producing a monocyclic aromatic hydrocarbon include a method of supporting boron on a crystalline aluminosilicate, a crystalline aluminogallosilicate, or a crystalline aluminozincosilicate with an ion exchange method or an impregnation method, a method of incorporating a boron compound at the time of zeolite synthesis to substitute a part of the skeleton of the crystalline aluminosilicate with boron, and a method of using a crystal accelerator containing boron at the time of zeolite synthesis.

The content of phosphorus and/or boron in the catalyst for producing a monocyclic aromatic hydrocarbon is preferably 0.1% to 10% by mass, more preferably 0.5% to 9% by mass, and still more preferably 0.5% to 8% by mass, in a case where the total of the catalyst is set to 100% by mass. In a case where the content of phosphorus and/or boron is 0.1% by mass or more, the yield decrease over time can be further prevented, and in a case where the content of phosphorus and/or boron is 10% by mass or less, the yield of the monocyclic aromatic hydrocarbon can be further increased.

(Shape)

The catalyst for producing a monocyclic aromatic hydrocarbon has, for example, a powder shape, a granule shape, a pellet shape, or the like, depending on the reaction type. For example, in a case of a fluidized bed type, the catalyst is made into a powder shape, and in a case of a fixed bed type, the catalyst is made into a granule shape or a pellet shape. The average particle size of the catalyst used in the fluidized bed type is preferably 30 to 180 µm and more preferably 50 to 100 µm. The bulk density of the catalyst that is used in the fluidized bed type is preferably 0.4 to 1.8 g/cc and more preferably 0.5 to 1.0 g/cc.

The average particle size indicates a particle size of 50% by mass in the particle size distribution which is obtained by sieving, and the bulk density is a value measured according to the method of JIS standard R9301-2-3.

In a case of obtaining a granule- or pellet-shaped catalyst, as necessary, an inert oxide as a binder may be added to a catalyst, and then molding may be carried out using various molding machines.

In a case where the catalyst for producing a monocyclic aromatic hydrocarbon contains an inorganic oxide such as a binder, a binder containing phosphorus may be used.

In the third embodiment, in the xylene conversion step, two molecules of aromatic hydrocarbons having a different number of carbon atoms can be converted to obtain two molecules of xylene by the transalkylation reaction.

Specifically, one molecule of toluene and one molecule of trimethylbenzene can be converted to obtain two molecules of xylene.

Further, in the third embodiment, the product in the cracking and reforming reaction step contains a heavy fraction having 9 or more carbon atoms. Since the heavy fraction having 9 or more carbon atoms serves as the starting raw material for the transalkylation reaction, xylene can be produced more efficiently.

EXAMPLES

Hereinafter, the present invention will be more specifically described according to Examples, but the present invention is not limited to Examples below.

Synthesis Example 1: Synthesis of Catalyst (X-1)

Both a solution (A) composed of 1,706.1 g of sodium silicate (J sodium silicate No. 3, $SiO_2$: 28% to 30% by mass, Na: 9% to 10% by mass, balance water, manufactured by Nippon Chemical Industrial Co., Ltd.) and 2227.5 g of water and a solution (B) composed of 64.2 g of $Al_2(SO_4)_3 \cdot 14$ to $18H_2O$ (special grade reagent, manufactured by FUJIFILM Wako Pure Chemical Corporation), 369.2 g of tetrapropylammonium bromide, 152.1 g of $H_2SO_4$ (97% by mass), 326.6 g of NaCl, and 2,975.7 g of water were prepared.

Then, the solution (B) was gradually added to the solution (A) while stirring the solution (A) at room temperature.

The resulting mixture was vigorously stirred with a mixer for 15 minutes to crush the gel into a milky, homogeneous, and fine state.

Next, the mixture was placed in a stainless steel autoclave, and the crystallization operation was carried out under self-pressure under the conditions of a temperature: 165° C., a time: 72 hours, and a stirring rate: 100 rpm. After completion of the crystallization operation, the product was filtered to recover a solid product, which was subsequently washed and filtered 5 times with about 5 liters of deionized water. The solid obtained by filtration was dried at 120° C. and further baked at 550° C. for 3 hours under air flow.

As a result of X-ray diffraction analysis (model name: Rigaku RINT-2500V), it was confirmed that the obtained baked product had an MR type structure. The $SiO_2/Al_2O_3$ ratio (molar ratio) determined by fluorescent X-ray analysis (model name: Rigaku ZSX101e) was 64.8. In addition, the aluminum element contained in the lattice skeleton, as calculated from this result, was 1.32% by mass.

A 30% by mass ammonium nitrate aqueous solution was added at a rate of 5 mL per 1 g of the obtained baked product, heated at 100° C. for 2 hours, stirred, filtered, and washed with water. After repeating this operation four times, drying was carried out at 120° C. for 3 hours to obtain an ammonium type crystalline aluminosilicate. Then, the obtained ammonium crystalline aluminosilicate was baked at 780° C. for 3 hours to obtain a proton type crystalline aluminosilicate.

Subsequently, 0.37 g of gallium nitrate was dissolved in 70 ml of distilled water and suspended so that an aqueous solution of 3.0% by mass (a value in a case where the total mass of ZSM-5 was 100% by mass) of gallium was ion-exchanged (or impregnated and supported) and stirred at 80° C. for 24 hours. Then, baking was carried out at 500° C. for 3 hours under air flow, thereby obtaining a gallium-containing crystalline aluminosilicate.

Next, 30 g of the obtained gallium-containing crystalline aluminosilicate was impregnated with 30 g of an aqueous diammonium hydrogen phosphate solution so that 0.2% by mass of phosphorus (the value in a case where the total weight of the catalyst was set to 100% by mass) was included and then subjected to drying at 120° C. Thereafter, after baking at 780° C. for 3 hours under air flow, a catalyst containing a gallium-containing crystalline aluminosilicate and phosphorus was obtained.

Tabletting molding was carried out by applying a pressure of 39.2 MPa (400 kgf) to the obtained catalyst, and coarse pulverization was carried out to adjust the size to 20 to 28 meshes, thereby obtaining a catalyst (X-1) of a granular material.

Synthesis Example 2: Synthesis of Catalyst (H-1)

Water glass No. 3 was added to 1 kg of an aqueous sodium aluminate solution having a concentration of 5% by mass, and the mixture was placed in a container kept at 70° C. Further, a solution prepared by adding an aqueous solution of titanium (IV) sulfate (24% by mass as the content of $TiO_2$) to 1 kg of an aqueous solution of aluminum sulfate having a concentration of 2.5% by mass was prepared in another container kept at 70° C., and this solution was dropwise added to the above-described aqueous solution containing sodium aluminate for 15 minutes. The amounts of the water glass and the aqueous titanium sulfate solution were adjusted so that the predetermined contents of silica and titania were achieved.

The end point of dropwise addition was at the time when the pH of the mixed solution reached 6.9 to 7.5, and the obtained slurry-like product was filtered through a filter to obtain a cake-like slurry. This cake-like slurry was transferred to a container equipped with a reflux condenser, 300 ml of distilled water and 3 g of a 27% aqueous ammonia solution were added to the container, and the mixture was heated and stirred at 70° C. for 24 hours. The slurry after the stirring treatment was placed in a kneading device, heated to 80° C. or higher, and kneaded while removing water to obtain a clay-like kneaded product.

The obtained kneaded product was extruded into a cylinder form having a diameter of 1.5 mm by an extrusion molding machine, dried at 110° C. for 1 hour, and then baked at 550° C. to obtain a molded carrier. 300 g of the obtained molded carrier was taken and impregnated while spraying with an impregnation solution prepared by adding molybdenum trioxide, cobalt (II) nitrate hexahydrate, and phosphoric acid (concentration: 85%) in 150 ml of distilled water and further adding malic acid until the mixture was dissolved.

The amounts of molybdenum trioxide, cobalt (II) nitrate hexahydrate, and phosphoric acid used were adjusted so that the predetermined amount of supported substance was achieved. The sample impregnated with the impregnation solution was dried at 110° C. for 1 hour and then baked at 550° C. to obtain a catalyst (H-1). The catalyst (H-1) had, based on the carrier, a $SiO_2$ content of 1.9% by mass and a $TiO_2$ content of 2.0% by mass, and based on the catalyst, an amount of supported $MoO_3$ of 22.9% by mass, an amount of supported CoO of 2.5% by mass, and an amount of supported $P_2O_5$ of 4.0% by mass.

<Production of Xylene (1)>

Examples 1 to 4

Using a flow type reaction device having a 5 mL reactor filled with the catalyst (X-1), the raw material shown in Table 1 below was brought into contact with the catalyst (X-1) to carry out the conversion reaction under the following conditions; a reaction temperature of 550° C., a reaction pressure of 0.1 MPaG, a nitrogen/raw material molar ratio of 1.0, and a contact time between raw material and catalyst of 6.4 seconds.

The conversion reaction was carried out under these conditions for 30 minutes to obtain a conversion reaction product containing a monocyclic aromatic hydrocarbon having 6 to 8 carbon atoms. Benzene, toluene, and xylene were separated and recovered from the obtained conversion reaction product. A disproportionation reaction product was obtained by subjecting the recovered toluene to the disproportionation reaction (catalyst: ZSM-5 (Si/Al=15, reaction temperature; 450° C., reaction pressure: 2.5 MPaG, WHSV: 4.5 $h^{-1}$, hydrogen/raw material molar ratio: 1.5) with a disproportionation reaction device.

The composition of the disproportionation reaction product was analyzed by an FID gas chromatograph directly connected to the disproportionation reaction device. Table 1 shows the yield of the monocyclic aromatic hydrocarbon having 6 to 8 carbon atoms in the entire process including the recycling of the unreacted toluene.

Comparative Examples 1 to 4

Using a flow type reaction device having a 5 mL reactor filled with the catalyst (X-1), the raw material oil shown in Table 2 below was brought into contact with the catalyst (X-1) to carry out the conversion reaction under the following conditions; a reaction temperature of 550° C., a reaction pressure of 0.1 MPaG, a nitrogen/raw material molar ratio of 1.0, and a contact time between raw material and catalyst of 6.4 seconds.

The conversion reaction was carried out under these conditions for 30 minutes to obtain a conversion reaction product containing a monocyclic aromatic hydrocarbon having 6 to 8 carbon atoms. The composition of the conversion reaction product was analyzed by an FID gas chromatograph directly connected to the flow type reaction device, and the yield of the monocyclic aromatic hydrocarbon having 6 to 8 carbon atoms was measured. The measurement results are shown in Table 2.

TABLE 1

|  |  | Example 1 | Example 2 | Example 3 | Example 4 |
|---|---|---|---|---|---|
| Raw material |  | Propane | Butane | Butene | Light naphtha |
| Yield | C7A | 0 | 0 | 0 | 0 |
| (% by weight) | C6A + C8A | 44 | 51 | 64 | 56 |

TABLE 2

|  |  | Comparative Example 1 | Comparative Example 2 | Comparative Example 3 | Comparative Example 4 |
|---|---|---|---|---|---|
| Raw material |  | Propane | Butane | Butene | Light naphtha |
| Yield | C7A | 18 | 23 | 24 | 21 |
| (% by weight) | C6A + C8A | 27 | 29 | 29 | 36 |

As shown in Tables 1 and 2 above, in Examples 1 to 4 to which the present invention was applied, the entire toluene was converted to benzene and xylene. As a result, it has been confirmed that the yields of benzene and xylene are improved in Examples 1 to 4 as compared with Comparative Examples 1 to 4 in which the disproportionation reaction is not carried out.

<Production of Xylene (2)>

Examples 5 to 8

Using a flow type reaction device (1) having a 5 mL reactor filled with the catalyst (X-1), the raw material oil shown in Table 3 below was brought into contact with the catalyst (X-1) to carry out the conversion reaction under the following conditions; a reaction temperature of 550° C., a reaction pressure of 0.1 MPaG, a nitrogen/raw material molar ratio of 1.0, and a contact time between raw material and catalyst of 6.4 seconds.

The conversion reaction was carried out under these conditions for 30 minutes to obtain a conversion reaction product (A) containing a monocyclic aromatic hydrocarbon having 6 to 8 carbon atoms.

In addition to the above conversion reaction, the raw material oil having the properties shown in Table 3 was subjected to the hydrogenation reaction (catalyst: catalyst (H-1), reaction temperature; 350° C., reaction pressure: 3.0 MPaG, LHSV: 0.5 $h^{-1}$, hydrogen/oil rate: 750 NL/L) in the hydrogenation reaction device to obtain a hydrogenated raw material oil.

Next, the hydrogenated raw material oil was brought into contact with the catalyst (X-1) under the conditions of a reaction temperature of 550° C., a reaction pressure of 0.1 MPaG, and a contact time of 30 seconds, where the contact time is for the contact with the zeolite component contained in the catalyst (X-1), and subjected to the cracking and reforming reaction to obtain a cracking and reforming reaction product (B-1) containing a monocyclic aromatic hydrocarbon having 6 to 8 carbon atoms.

The obtained (A) and (B-1) were mixed and then distilled to separate them into benzene, toluene, xylene, C9 aroma, and a heavy component. The recovered toluene and the C9 aroma were subjected to the transalkylation reaction in the transalkylation reaction device (catalyst: a solid acid catalyst composed of mordenite on which 2% by mass of rhenium (Re) has been supported in terms of metal, reaction temperature: 400° C., reaction pressure: 3.0 MPaG, WHSV: 1.0 $h^{-1}$, hydrogen/raw material molar ratio: 5.0) to obtain a transalkylation reaction product (C).

On the other hand, the heavy component recovered by distillation of the mixture of (A) and (B-1) was subjected to the hydrogenation reaction and the cracking and reforming reaction again under the same reaction conditions as described above to obtain a cracking and reforming reaction product (B-2). After mixing (B-2) and (C), composition analysis was carried out by an RD gas chromatograph. Table 4 shows the yield of the monocyclic aromatic hydrocarbon having 6 to 8 carbon atoms in the entire process.

Comparative Examples 5 to 8

Using a flow type reaction device (1) having a 5 mL reactor filled with the catalyst (X-1), the raw material oil shown in Table 4 below was brought into contact with the catalyst (X-1) to carry out the conversion reaction under the following conditions; a reaction temperature of 550° C., a reaction pressure of 0.1 MPaG, a nitrogen/raw material molar ratio of 1.0, and a contact time between raw material and catalyst of 6.4 seconds.

The conversion reaction was carried out under these conditions for 30 minutes to obtain a conversion reaction product (A') containing a monocyclic aromatic hydrocarbon having 6 to 8 carbon atoms.

In addition to the above conversion reaction, the raw material oil having the properties shown in Table 3 was subjected to the hydrogenation reaction (catalyst: catalyst (H-1), reaction temperature; 350° C., reaction pressure: 3.0 MPaG, LHSV: 0.5 $h^{-1}$, hydrogen/oil rate: 750 NL/L) in the hydrogenation reaction device to obtain a hydrogenated raw material oil.

Next, the hydrogenated raw material oil was brought into contact with the catalyst (X-1) under the conditions of a reaction temperature of 550° C., a reaction pressure of 0.1 MPaG, and a contact time of 30 seconds, where the contact time is for the contact with the zeolite component contained in the catalyst (X-1), and subjected to the cracking and reforming reaction to obtain a cracking and reforming reaction product (B-1') containing a monocyclic aromatic hydrocarbon having 6 to 8 carbon atoms.

The obtained (A') and (B-1') were mixed and then distilled to separate them into benzene, toluene, xylene, C9 aroma, and a heavy component. The recovered heavy component was subjected to the hydrogenation reaction and the cracking and reforming reaction again under the same reaction conditions as described above to obtain a cracking and reforming reaction product (B-2'). The composition of B-2' was analyzed by an FID gas chromatograph. Table 5 shows the yield of the monocyclic aromatic hydrocarbon having 6 to 8 carbon atoms in the entire process.

TABLE 3

| Property of raw material |  | Analysis method |
|---|---|---|
| Density g/cm$^3$ (measurement temperature: 15° C.) | 0.908 | JIS K 2249 |
| Kinematic viscosity mm$^2$/s (measurement temperature: 30° C.) | 3.645 | JIS K 2283 |

TABLE 3-continued

|  | Property of raw material |  |  | Analysis method |
|---|---|---|---|---|
| Distillation property | Initial boiling point | °C. | 177.5 | JIS K 2254 |
|  | 10% by volume distilling temperature | °C. | 226.5 |  |
|  | 50% by volume distilling temperature | °C. | 276.0 |  |
|  | 90% by volume distilling temperature | °C. | 350.0 |  |
|  | End point | °C. | 377.0 |  |
| Composition analysis | Saturated component | % by volume | 34 | JPI-5S-49 |
|  | Olefin component | % by volume | 8 |  |
|  | Entire aromatic component | % by volume | 58 |  |
|  | Monocyclic aromatic component | % by volume | 23 |  |
|  | Bicyclic aromatic component | % by volume | 26 |  |
|  | Tricyclic or more cyclic aromatic component | % by volume | 9 |  |

TABLE 4

|  |  | Example 5 | Example 6 | Example 7 | Example 8 |
|---|---|---|---|---|---|
| Raw material (% by weight) |  | Propane 50 raw material oil (Table 3) 50 | Butane 50 raw material oil (Table 3) 50 | Butene 50 raw material oil (Table 3) 50 | Light naphtha 50 raw material oil (Table 3) 50 |
| Yield (% by weight) | C7A | 0 | 0 | 0 | 0 |
|  | C6A + C8A | 56 | 60 | 66 | 62 |

TABLE 5

|  |  | Comparative Example 5 | Comparative Example 6 | Comparative Example 7 | Comparative Example 8 |
|---|---|---|---|---|---|
| Raw material (% by weight) |  | Propane 50 raw material oil (Table 3) 50 | Butane 50 raw material oil (Table 3) 50 | Butene 50 raw material oil (Table 3) 50 | Light naphtha 50 raw material oil (Table 3) 50 |
| Yield (% by weight) | C7A | 26 | 28 | 33 | 27 |
|  | C6A + C8A | 32 | 34 | 35 | 37 |

As shown in Tables 4 and 5 above, in Examples 5 to 8 to which the present invention is applied, the entire toluene is converted to benzene and xylene. As a result, in Examples 5 to 8, it has been confirmed that the yields of benzene and xylene are improved as compared with Comparative Examples 5 to 8 in which the transalkylation reaction is not carried out.

REFERENCE SIGNS LIST

1: Raw material containing a light hydrocarbon having 2 to 7 carbon atoms as the main component
2: Conversion reaction device
3: Regenerator
4: Gas-liquid separator
5: Disproportionation reaction device
6: Transalkylation reaction device
7: Raw material oil
8: Hydrogenation device
9: Cracking and reforming reaction device

What is claimed is:

1. A method for producing xylene, comprising:
   conducting a conversion reaction by bringing a raw material containing a light hydrocarbon having 2 to 7 carbon atoms as a main component into contact with a crystalline aluminosilicate-containing catalyst (Z) to produce a product containing a monocyclic aromatic hydrocarbon having 6 to 8 carbon atoms by cyclodehydrogenation; and
   conducting a xylene conversion by subjecting the product to a disproportionation reaction or a transalkylation reaction.

2. The method for producing xylene according to claim 1, further comprising conducting a cracking and reforming reaction by bringing a raw material oil having a 10% by volume distilling temperature of 140° C. or higher and a 90% by volume distilling temperature of 380° C. or lower into contact with a crystalline aluminosilicate- containing catalyst (F) to produce the product containing a monocyclic aromatic hydrocarbon having 6 to 8 carbon atoms.

3. The method for producing xylene according to claim 1, wherein the xylene conversion includes subjecting the product to a disproportionation reaction.

4. The method for producing xylene according to claim 1, wherein the xylene conversion includes subjecting the product to a transalkylation reaction.

5. The method for producing xylene according to claim 1, wherein a catalyst that is used in the xylene conversion step includes ZSM-5, a mordenite zeolite, or a beta zeolite.

6. The method for producing xylene according to claim 1, wherein a content of gallium with respect to 100 parts by mass of a catalyst composition of the catalyst that is used in the conversion reaction step is 0.1 parts by mass or more and 10.0 parts by mass or less.

7. The method for producing xylene according to claim 1, further comprising:
   hydrogenating a raw material oil having a 10% by volume distilling temperature of 140° C. or higher and a 90% by volume distilling temperature of 380° C. or lower to obtain a hydrogenated oil, and conducting a cracking and reforming reaction by bringing the hydrogenated oil into contact with a crystalline aluminosilicate-containing catalyst (F) to produce the product containing a monocyclic aromatic hydrocarbon having 6 to 8 carbon atoms.

8. The method for producing xylene according to claim 2, wherein the xylene conversion includes subjecting the product to a transalkylation reaction.

9. The method for producing xylene according to claim 7, wherein the xylene conversion includes subjecting the product to a transalkylation reaction.

10. A method for producing xylene, comprising:

conducting a conversion reaction by bringing a raw material containing a light hydrocarbon having 2 to 7 carbon atoms as a main component into contact with a crystalline aluminosilicate-containing catalyst (Z) on which gallium and phosphorus are supported to produce a product containing a monocyclic aromatic hydrocarbon having 6 to 8 carbon atoms; and conducting a xylene conversion by subjecting the product to a disproportionation reaction or a transalkylation reaction.

11. A method for producing xylene, comprising:

conducting a conversion reaction by bringing a raw material containing a light hydrocarbon having 2 to 7 carbon atoms as a main component into contact with a crystalline aluminosilicate-containing catalyst (Z) to produce a product containing a monocyclic aromatic hydrocarbon having 6 to 8 carbon atoms by cyclodehydrogenation; and conducting a xylene conversion by subjecting the product to a disproportionation reaction or a transalkylation reaction in the presence of a catalyst consisting of a crystalline aluminosilicate.

* * * * *